US011883538B2

(12) United States Patent
Nardi Ricart et al.

(10) Patent No.: US 11,883,538 B2
(45) Date of Patent: Jan. 30, 2024

(54) SUSTAINED RELEASE COMPOSITIONS COMPRISING MICRONIZED TOLCAPONE

(71) Applicant: Som Innovation Biotech, S.L., Barcelona (ES)

(72) Inventors: Anna Nardi Ricart, Barcelona (ES); Josep María Suñé Negre, Barcelona (ES); Núria Reig Bolaño, Barcelona (ES); Raúl Insa Boronat, Barcelona (ES); Oscar Huertas Gambín, Barcelona (ES); Santiago Esteva Gras, Barcelona (ES); Gal·la Pericot Mohr, Barcelona (ES)

(73) Assignee: Som Innovation Biotech, S.L., Barcelona (ES)

( * ) Notice: Subject to any disclaimer, the term of this patent is extended or adjusted under 35 U.S.C. 154(b) by 0 days.

(21) Appl. No.: 16/321,336

(22) PCT Filed: Jul. 28, 2017

(86) PCT No.: PCT/EP2017/069168
§ 371 (c)(1),
(2) Date: Jan. 28, 2019

(87) PCT Pub. No.: WO2018/019997
PCT Pub. Date: Feb. 1, 2018

(65) Prior Publication Data
US 2019/0167596 A1 Jun. 6, 2019

(30) Foreign Application Priority Data

Jul. 29, 2016 (EP) .................. 16382372.7

(51) Int. Cl.
*A61K 9/20* (2006.01)
*A61K 31/122* (2006.01)
*A61K 31/12* (2006.01)

(52) U.S. Cl.
CPC .......... *A61K 9/2054* (2013.01); *A61K 9/2009* (2013.01); *A61K 9/2013* (2013.01); *A61K 9/2095* (2013.01); *A61K 31/12* (2013.01); *A61K 31/122* (2013.01)

(58) Field of Classification Search
CPC .. A61K 9/2054; A61K 9/2009; A61K 9/2013; A61K 9/2095; A61K 31/12; A61K 31/122; A61P 25/16; A61P 43/00
See application file for complete search history.

(56) References Cited

U.S. PATENT DOCUMENTS

| 2007/0003619 | A1* | 1/2007 | Smith ..................... A61K 9/14 424/469 |
| 2010/0112053 | A1 | 5/2010 | Momose et al. |
| 2013/0195973 | A1* | 8/2013 | Gupta ................. A61K 9/4808 424/452 |
| 2014/0296188 | A1 | 10/2014 | Centellas Casado et al. |
| 2016/0278899 | A1* | 9/2016 | Heller ................. A61C 19/063 |

FOREIGN PATENT DOCUMENTS

| WO | WO 97/44022 | 11/1997 |
| WO | WO 99/52504 | 10/1999 |
| WO | WO-2016036308 A1 * | 3/2016 ........... A61K 31/165 |

OTHER PUBLICATIONS

International Search Report for PCT/EP27/069168, dated Sep. 28, 2017.
"Tasmar 100mg" In: Rote Lists 2012, Jan. 2, 2012.

* cited by examiner

*Primary Examiner* — Mark V Stevens
*Assistant Examiner* — Nathan W Schlientz
(74) *Attorney, Agent, or Firm* — King & Spalding

(57) ABSTRACT

The present invention relates to sustained release tablet comprising micronized tolcapone, a release retardant and a binder, to said tablet for use in the prevention and/or treatment of a transthyretin-associated amyloidosis, to a method for the prevention and/or treatment of a transthyretin-associated amyloidosis comprising administering to a subject in need thereof an effective amount of said tablet, to pharmaceutical composition in the form of said tablet which is used in the prevention and/or treatment of a transthyretin-associated amyloidosis and to a process for the manufacture of said tablet.

10 Claims, 1 Drawing Sheet

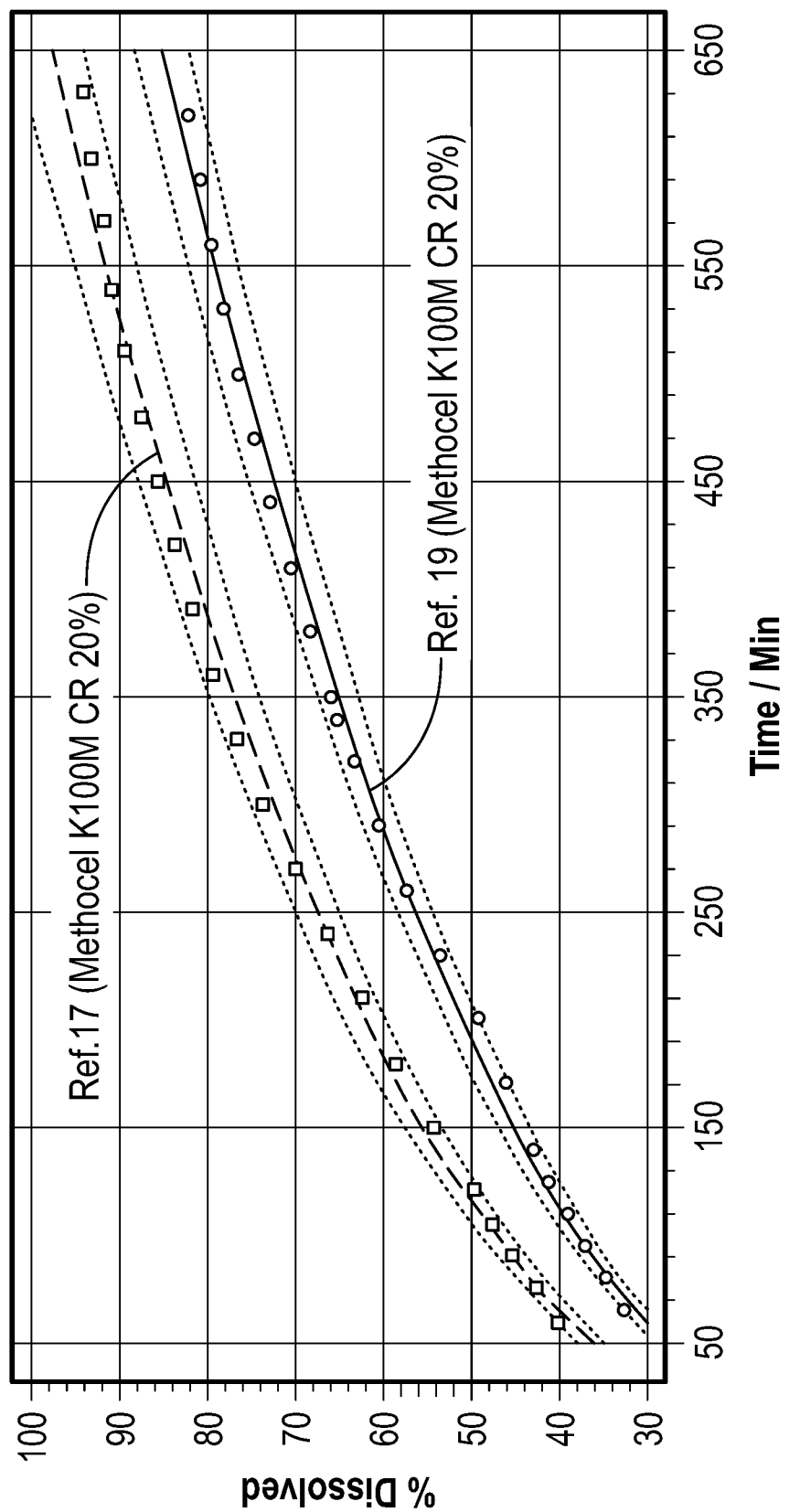

SUSTAINED RELEASE COMPOSITIONS COMPRISING MICRONIZED TOLCAPONE

CROSS REFERENCE TO RELATED APPLICATIONS

This application is a national phase application under 35 U.S.C. § 371 of International Application No. PCT/EP2017/069168, filed on 28 Jul. 2017, which claims the benefit of European Patent Application No. 16382372.7, filed 29 Jul. 2016. The complete disclosure of each of the above-identified applications is fully incorporated herein by reference.

FIELD OF THE INVENTION

The present invention relates to sustained release compositions comprising micronized tolcapone.

The therapeutic compound (3,4-dihydroxy-5-nitrophenyl)(4-methylphenyl)methanone, more commonly known as tolcapone, is described in U.S. Pat. No. 5,236,952.

The currently marketed formulations of tolcapone are 100 mg and 200 mg film coated tablets. Tolcapone is marketed in many countries under the brand name TASMAR®. TASMAR® is a tablet which is used by oral administration. Said tablet is manufactured through a process involving the granulation of tolcapone and the subsequent mixture of said granules with extragranular excipients. The mixture is then compressed into an immediate release tablet.

There is a need for an extended release tablet comprising tolcapone, for example, to reduce peak plasma concentration and to maintain therapeutic plasma levels for a prolonged period of time. In particular, there is a need for an extended release tablet comprising tolcapone which may be manufactured by a direct compression process, i.e. a process that does not involve the preparation of granules comprising tolcapone and other excipients and the subsequent mixture of said granules with extragranular excipients prior to compression into tablets.

It is an object of the present invention to provide for a sustained release formulation for tolcapone, preferably in the form of a tablet. It is a further object of the present invention to provide for a sustained release formulation in the form of a tablet manufactured by using a direct compression process. It is another object of the present invention to provide for a method for the prevention and/or treatment of a transthyretin-associated amyloidosis comprising administering to a subject in need thereof the sustained release formulation of tolcapone. It is still another object of the present invention to provide for the use of micronized tolcapone together with a release retardant and a binder for the manufacture of a medicament in the form of a tablet for the treatment of a transthyretin-associated amyloidosis. It is still another object of the present invention to provide for a pharmaceutical composition in the form of a sustained release tablet which is used in the prevention and/or treatment of a transthyretin-associated amyloidosis.

Surprisingly, it has been found that micronized tolcapone may provide advantages for the formulation of a sustained release composition since, quite unexpectedly, compositions comprising micronized tolcapone show a slower release of the active ingredient than identical compositions wherein tolcapone is incorporated in a non-micronized form.

This is completely unexpected since it is very well known that reduction of the particle size of a product, for example by micronization, results in an increase of the product's specific surface area and, consequently, in an increase of the dissolution rate of said product.

Among the advantages of using micronized tolcapone in compositions designed for the sustained release of said tolcapone one can cite that the time necessary for the release of 80% of the product may be extended in comparison with identical formulations wherein tolcapone is used in non-micronized form.

SUMMARY OF THE INVENTION

In a first aspect, the present invention relates to modified release tablets that contain tolcapone in micronized form. The amount of tolcapone in the tablets can range from 5 to 80% by weight of the composition. The balance of the tablet can be made up of at least one release retardant. In a particular aspect of the present invention the release retardant is a water-soluble, water swellable and/or water insoluble polymer. Particularly useful as release retardants are cellulose polymers such as ethylcellulose, hydroxypropyl cellulose and/or hydroxypropyl methyl cellulose. The aforementioned tablets can advantageously be prepared through a direct compression process.

In a second aspect of the present invention, the invention features a method for making sustained release tablets of tolcapone. In a particular embodiment, tolcapone is mixed with a release retardant and optionally other pharmaceutically acceptable excipients using any mixing equipment such a biconical drum. The resulting mixture can be compressed into tablets.

In third aspect the present invention relates to a method for the prevention and/or treatment of a transthyretin-associated amyloidosis comprising administering to a subject in need thereof an effective amount of a tablet according to the first aspect described above.

In a fourth aspect the present invention relates to the use of micronized tolcapone together with a release retardant and a binder for the manufacture of a medicament in the form of a tablet as defined in the first aspect for the treatment of a transthyretin-associated amyloidosis.

In a fourth aspect the present invention relates to a pharmaceutical composition in the form of a tablet as defined in the first aspect which is used in the prevention and/or treatment of a transthyretin-associated amyloidosis.

BRIEF DESCRIPTION OF THE FIGURES

The accompanying figures, which are incorporated in and constituting a part of the specification, illustrates exemplary embodiments of the present invention.

FIG. 1 shows a chart depicting the dissolution profiles for exemplary embodiments in accordance with the present invention as disclosed in Examples 3 and 4.

DETAILED DESCRIPTION OF THE INVENTION

The present invention relates to sustained release tablets of tolcapone which comprise tolcapone, a release retardant and to a process for preparing such tablets. The sustained release tablets may optionally further comprise binders, plasticizers, disintegrants, and/or lubricants.

As used herein the term "tablet" is intended to encompass compressed pharmaceutical dosage formulations of all shapes and sizes, whether uncoated or coated.

As used herein the term "pharmaceutically acceptable" refers to those compounds, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio. In particular any compound which has been approved for human or veterinary use is a "pharmaceutically acceptable" compound.

As used herein the term "tolcapone" refers to the free phenolic form of tolcapone or a pharmaceutically acceptable salt thereof.

As used herein the terms "tolcapone in micronized form" and "micronized tolcapone" are used indistinctively to designate a solid form of tolcapone having a $D_{v,0.9}$ of not more than 70 µm, preferably not more than 60 µm and most preferably not more than 55 µm. $D_{v,0.9}$ may be determined according to the general method described in section 2.9.31 of the European Pharmacopeia in particular using a particle size laser analyzer MASTERSIZER 2000 from Malvern featuring a wet dispersion unit HYDRO 2000 SM for small volumes of sample.

Tolcapone is present in the tablets of the present invention in a therapeutically effective amount or concentration. Such a therapeutically effective amount or concentration is known to one of ordinary skill in the art as the amount or concentration varies with the therapeutic compound being used and the indication which is being addressed. For example, in accordance with the present invention, Tolcapone may be present in an amount of 5% to 80% by weight of tablet. In one embodiment, Tolcapone may be present in an amount by weight of 10% to about 70% by weight of tablet. In one embodiment, tolcapone may be present in an amount by weight of about 20% to about 60% by weight of tablet. In one embodiment, tolcapone may be present in an amount by weight of about 30% to about 50% by weight of tablet.

As used herein, the term "sustained release" refers to the gradual but continuous or sustained release over a relatively extended period of tolcapone content after oral ingestion such as a slow release of tolcapone, e.g., not greater than 90%, preferably not greater than 80% within a relatively long period of time, e.g., within 3 hour, preferably 4 hours and more preferably 5 hours after oral ingestion. Particularly useful conditions for sustained release are release of not greater than 90% of tolcapone within 5 hours after oral ingestion.

Since measurement of the release of tolcapone from a tablet after oral ingestion is difficult, for the purpose of the present invention, a tablet is considered to exhibit a "sustained release" profile when the proportion of tolcapone dissolved after 5 hours in the conditions of USP36 Tolcapone monograph is not higher than 90%, preferably not higher than 80% of the total amount of tolcapone in the tablet.

As used herein the term "release retardant" refers to any material or substance that slows the release of tolcapone from a tablet when orally ingested. A release retardant is typically a cellulose polymer.

As used herein the term "cellulose polymer" refers to cellulose esters and cellulose ethers (e.g., methylcellulose and ethylcellulose) hydroxyalkylcelluloses (e.g., -hydroxypropylcellulo se), hydroxyalkylalkylcelluloses (e.g., hydroxypropylmethylcellulose), cellulose phthalates (e.g., cellulose acetate phthalate and hydroxypropylmethylcellulose phthalate) and cellulose succinates (e.g., hydroxypropylmethylcellulose succinate or hydroxypropylmethylcellulose acetate succinate).

In an embodiment of the present invention the "release retardant" is hydroxypropylmethylcellulose.

As used herein the term "direct compression" refers to a tabletting process wherein the tablet or any other compressed dosage form is made by a process comprising the steps of dry blending the components of the formulation and compressing the dry blend to form the formulation.

As used herein the term "suitable mixing equipment" is used to designate an equipment which may be used to blend solid ingredients in the absence of any liquid or fluid ingredient. Examples of such equipment are a ribbon blender, a V blender, a cone screw blender, a screw blender, a double cone blender, a planetary mixer, a paddle mixer, a drum blender, a high shear mixer and a biconical drum.

As used herein, the term "direct compression" refers to the following compounding process that comprises the steps of:
(a) providing two or more solid components (such as tolcapone, at least one release retardant, and optionally, a binder, a lubricant and other pharmaceutically acceptable excipients)
(b) forming a mixture with the components of step (a) using any suitable mixing equipment in the absence of any liquid ingredient.
(c) filing the mixture of step (b) into a die and compressing it using a punch.

As used herein the term "solid" is used to designate any material which is solid at room temperature (25° C.).

As used herein the term "liquid" is used to designate any material which is liquid at room temperature (25° C.).

Examples of pharmaceutically acceptable binders include, but are not limited to, starches; celluloses and derivatives thereof, for example, microcrystalline cellulose, e.g., AVICEL PH from FMC (Philadelphia, PA), sucrose; dextrose; corn syrup; polysaccharides; and gelatin. The binder may be present in an amount from about 0% to about 65%, e.g., 20-50% by weight of the composition.

Examples of pharmaceutically acceptable lubricants include, but are not limited to, colloidal silica, magnesium trisilicate, starches, talc, tribasic calcium phosphate, magnesium stearate, aluminum stearate, calcium stearate, magnesium carbonate and magnesium oxide. The lubricant may be present in an amount from about 0% to about 5% by weight of the composition. In one embodiment, the lubricant may be present in an amount from about 0.1% to about 1.5% by weight of composition.

In an embodiment of the present invention the tablet comprises a cellulose polymer, preferably selected from the group consisting of cellulose ethers and cellulose esters, more preferably hydroxypropyl methyl cellulose, as release retardant.

In another embodiment of the present invention the tablet comprises microcrystalline cellulose as a binder.

In another embodiment of the present invention the tolcapone used in the manufacture of the tablet has a particle size distribution characterized in that its $D_{v,0.9}$ is not greater than 70 µm.

In another embodiment of the present invention the tablet comprises from 5% to 80% by weight of tolcapone.

In another embodiment of the present invention the tablet is characterized in that the proportion of tolcapone dissolved after 5 hours in the conditions of USP36 Tolcapone monograph is not higher than 90% of the total amount of tolcapone in the tablet.

In another embodiment of the present invention the tablet is characterized in that it shows a release of tolcapone such that not greater than 90% is released during the period starting with oral ingestion and ending 5 hours after oral ingestion.

In another embodiment of the present invention the tolcapone used in the manufacture of the tablet has a particle size distribution characterized in that its $D_{v,0.5}$ is greater than 10 µm but not greater than 80 µm.

In another embodiment of the present invention the tablet comprises tolcapone, hydroxypropylmethyl cellulose and microcrystalline cellulose.

In another embodiment of the present invention the tablet comprises tolcapone, hydroxypropylmethyl cellulose, microcrystalline cellulose, talc, magnesium stearate and anhydrous colloidal silica.

In an embodiment of the present invention the tablets comprise:
   a) 5 to 80% by weight, for example 14 to 41% by weight of tolcapone
   b) 20 to 36% of hydroxypropylmethyl cellulose such as, for example, Methocel® K 100 M
   c) 8 to 65% by weight, for example 36 to 49% by weight of microcrystalline cellulose such as, for example, Vivapur® 102
   d) 0.1 to 3% by weight, for example 0.1 to 1.4% by weight of talc
   e) 0.03 to 2% by weight, for example 0.03 to 0.7% by weight of magnesium stearate
   f) 0.06 to 0.8% by weight for example 0.26 to 0.42% by weight of anhydrous colloidal silica In an embodiment of the present invention the tablets weight from 750 to 850 mg and comprise:
   a) 50 to 500 mg, for example 250 to 350 mg of tolcapone
   b) 160 to 280 mg, for example 160 to 260 mg of hydroxypropylmethyl cellulose such as, for example, Methocel® K 100 M
   c) 50 to 500 mg, for example 260 to 350 mg of microcrystalline cellulose such as, for example, Vivapur® 102
   d) 0.1 to 20 mg, for example 0.1 to 10 mg of talc
   e) 0.2 to 10 mg, for example 0.4 to 6 mg of magnesium stearate
   f) 0.6 to 6 mg, for example 2 to 3 mg of anhydrous colloidal silica In another aspect the present invention relates to a tablet as previously defined for use in the prevention and/or treatment of a transthyretin-associated amyloidosis, such as familial amyloid polyneuropathy, senile systemic amyloidosis, leptomeningeal amyloidosis, familial amyloid cardiomyopathy.

In another aspect the present invention relates to a process for the manufacture of a tablet as defined before comprising the steps:
   a) providing tolcapone, a release retardant and a binder
   b) optionally sieving the ingredients of step a) with a mesh having 5 mm openings
   c) mixing the ingredients of step b)
   d) compressing the ingredients of step c) to form tablets.

EXAMPLES

Determination of Tolcapone's Particle Size

Particle size measurement ($D_{v,0.1}$, $D_{v,0.5}$, $D_{v,0.9}$ and $D_{v,1.0}$) may be determined according to the general method described in section 2.9.31 of the European Pharmacopeia in particular using a particle size laser analyzer MASTERSIZER 2000 from Malvern featuring a wet dispersion unit HYDRO 2000 SM for small volumes of sample.
Material:
Sample: Tolcapone suspension
Refraction index: 1.59 (default)
Dispersant: water for injection
Refraction index: 1.33

Cycles:
Measurements for each aliquot: 3
Lag time: 12 s
Pump stirring velocity: 2500 rpm
Measuring Time:
Measure: 12 s (in triplicates)
Measure snaps: 12000
Background: 10 s
Background snaps: 10000
Three readings are made for each sample.
Solubility Measurements Solubility measurements are carried out using the protocol described in US Pharmacopeia USP 36 with minor changes, such as longer time points.

The specific conditions used in the measurements were:
Medium: 900 ml of a phosphate buffer with a pH of 6.8 containing 1% of sodium lauryl sulfate.
Apparatus 2: at 75 rpm
Time: at various intervals between 0 and 1440 minutes
Procedure: Determine the amount of Tolcapone dissolved by employing UV absorption at the wavelength of maximum absorbance at about 271 nm on filtered portions of the solution under test, suitably diluted with Medium, if necessary, in comparison with a Standard solution having a known concentration of USP Tolcapone RS in the same Medium. Calculate the amount of tolcapone dissolved in each Tablet.
General.

In the following examples the sustained release tablets are prepared using the following process:
1. The ingredients are weighed
2. The ingredients are sieved with a mesh with 5 mm openings
3. The ingredients are mixed in a biconical drum at a rotation speed of 20 rpm during 10 minutes
4. 800 mg of the resulting mixture are compressed in an eccentric tableting press BONALS with oblong punches measuring 19 mm×10 mm without slot.

In the following examples the particle size distribution of non-micronized tolcapone is characterized by the following parameters

| $D_{v,0.1}$ | $D_{v,0.5}$ | $D_{v,0.9}$ | $D_{v,1.0}$ |
|---|---|---|---|
| <22.45 µm | <87.23 µm | <307.86 µm | <1096.48 µm |

In the following examples the particle size distribution of micronized tolcapone is characterized by the following parameters

| $D_{v,0.1}$ | $D_{v,0.5}$ | $D_{v,0.9}$ | $D_{v,1.0}$ |
|---|---|---|---|
| <6.09 µm | <17.62 µm | <54.33 µm | <316.23 µm |

$D_{v,x}$ value indicates that x*100% of the volume of the particles is in particles which are smaller than this value. Thus, $D_{v,0.9}$ lower than 54.33 µm that 90% of the volume of the particles is in particles which are smaller 54.33 µm.

Example 1

| Components | weight % | weight (mg) |
|---|---|---|
| Tolcapone | 37.5 | 300 |
| Hydroxypropylmethyl | 29.0 | 232 |

| Components | weight % | weight (mg) |
| --- | --- | --- |
| cellulose[1] | | |
| Microcrystalline cellulose[2] | 31.7 | 253.60 |
| Talc | 1.0 | 8 |
| Magnesium stearate | 0.5 | 4 |
| Anhydrous colloidal silica[3] | 0.3 | 2.4 |
| TOTAL | 100 | 800 |

[1]Methocel ® K 100 M CR
[2]Vivapur ® 102
[3]Aerosil ® 200

Example 2

| Components | weight % | weight (mg) |
| --- | --- | --- |
| Tolcapone | 37.5 | 300 |
| Hydroxypropylmethyl cellulose[1] | 20 | 160 |
| Microcrystalline cellulose[2] | 42.03 | 336.24 |
| Talc | 0.12 | 0.96 |
| Magnesium stearate | 0.05 | 0.4 |
| Anhydrous colloidal silica[3] | 0.3 | 2.4 |
| TOTAL | 100 | 800 |

[1]Methocel ® K 100 M CR
[2]Vivapur ® 102
[3]Aerosil ® 200

Example 3

| Components | weight % | weight (mg) |
| --- | --- | --- |
| Tolcapone (non-micronized) | 37.5 | 300 |
| Hydroxypropylmethyl cellulose[1] | 20.0 | 160 |
| Microcrystalline cellulose[2] | 42.03 | 336.24 |
| Talc | 0.12 | 0.96 |
| Magnesium stearate | 0.05 | 0.4 |
| Anhydrous colloidal silica[3] | 0.30 | 2.4 |
| TOTAL | 100 | 800 |

[1]Methocel ® K 100 M CR
[2]Vivapur ® 102
[3]Aerosil ® 200

Example 4

| Components | weight % | weight (mg) |
| --- | --- | --- |
| Tolcapone (micronized) | 37.5 | 300 |
| Hydroxypropylmethyl cellulose[1] | 20.0 | 160 |
| Microcrystalline cellulose[2] | 42.03 | 336.24 |
| Talc | 0.12 | 0.96 |
| Magnesium stearate | 0.05 | 0.4 |
| Anhydrous colloidal silica[3] | 0.30 | 2.4 |
| TOTAL | 100 | 800 |

[1]Methocel ® K 100 M CR
[2]Vivapur ® 102
[3]Aerosil ® 200

Example 5

Dissolution Profiles of the Compositions of Example 3 and 4

Solubility measurements were carried out following the protocol described above under the heading "Solubility measurements". The data obtained were processed by s simple regression method adjusting these data to a potential equation $[Y(\% \text{ dissolved}) = A \cdot X(\text{time})^B]$ which is optimal to explain the evolution of the dissolution process within a bounded time interval (50 to 650 minutes).

The results obtained are as follows:

Product of Example 3

Adjusted equation: $Y = 2.0656 \cdot X^{0.3887}$

| Regression analysis-Multiplicative model: Y = a * X^b | | | | |
| --- | --- | --- | --- | --- |
| Dependent variable: (Comp3) Independent variable: (Time3) Selection variable: Time3 > 50 & Time3 < 650 | | | | |
| Parameter | Estimation | Standard Error | Statistical T | P-Value |
| Ordinate | 2.06557 | 0.0289582 | 71.3295 | 0.0000 |
| Slope | 0.388712 | 0.00516411 | 75.2719 | 0.0000 |
| Analysis of Variance | | | | |
| Source | Square sum | GL | Average squar | F-ratio | P-Value |
| Model | 1.67318 | 1 | 1.67318 | 5665.86 | 0.0000 |
| Residue | 0.00590618 | 20 | 0.000295309 | | |
| Total (Corr.) | 1.67909 | 21 | | | |

Correlation coefficient = 0.99824
Square-R = 99.6483 percentage

From the results of the analysis of variance (ANOVA) of the adjusted model it is observed that this explains the 99.65% of the quadratic variation of dissolution as a function of time, resulting in a correlation coefficient r=0.9982 between the observed values and values adjusted with the help of the equation. Thus, it may be concluded that the dissolution kinetic of the product of example 3 fits a mathematical model of simple potential regression with a coefficient A=2.0656 and a power B=0.3887.

Product of Example 4

Adjusted equation: $Y=1.6295 \cdot X^{0.4347}$

| Regression analysis-Multiplicative model: Y = a * X^b | | | | |
|---|---|---|---|---|
| Dependent variable: (Comp4) Independent variable: (Time4) Selection variable: Time4 > 50 & Time4 < 650 | | | | |
| Parameter | Estimation | Standard Error | Statistical T | P-Value |
| Ordinate | 1.62945 | 0.0287 | 56.7753 | 0.0000 |
| Slope | 0.434735 | 0.00513096 | 84.7279 | 0.0000 |
| Analysis of Variance | | | | |
| Source | Square sum | GL | Average squar | F-ratio P-Value |
| Model | 1.95026 | 1 | 1.95026 | 7178.81 0.0000 |
| Residue | 0.00543337 | 20 | 0.000271669 | |
| Total (Corr.) | 1.95569 | 21 | | |

Correlation coefficient = 0.99861
Square-R = 99.7222 percentage

From the results of the analysis of variance (ANOVA) of the adjusted model it is observed that this explains the 99.72% of the quadratic variation of dissolution as a function of time, resulting in a correlation coefficient r=0.9986 between the observed values and values adjusted with the help of the equation. Thus, it may be concluded that the dissolution kinetic of the product of example 4 fits a mathematical model of simple potential regression with a coefficient A=1.6295 and a power B=0.4347.

Comparison Between the Dissolution Profiles of the Compositions of Examples 3 and 4 Adjusted to the Potential Lineal Regression A comparative statistical study is carried out based on confidence intervals at 95% for each experimental value to determine whether there exist statistically significant differences between the kinetics of dissolution of the formulations of examples 3 and 4 within the time interval of 50 minutes to 650 minutes. Insofar as these intervals do not overlap each other (which can be seen when plotting said prediction intervals), it can be concluded that there are significant differences between the kinetics of dissolution obtained for each of the formulations.

The representation of the experimental values and the adjusted models and prediction intervals for a confidence interval of 95% is presented in FIG. 1.

It is noted that for the entire experimental range studied, the adjusted dissolution values for the composition of example 3 are, with a confidence interval of 95%, higher than those for the composition of example 4. Thus, it may be concluded that the composition of example 3 (comprising non-micronized tolcapone) shows a higher dissolution rate than that of the composition of example 4 (comprising micronized tolcapone).

The invention claimed is:

1. A sustained release solid tablet for oral administration comprising (a) from 50-500 mg and from about 30% to about 50% by weight of the tablet micronized tolcapone having a $D_{v,0.9}$ of not more than 55 μm, (b) a cellulose polymer and (c) a binder, wherein the tablet is coated and compressed and the proportion of tolcapone dissolved after 5 hours in the conditions of USP36 Tolcapone monograph is not higher than 90% of the total amount of tolcapone in the tablet.

2. A tablet according to claim 1 wherein the cellulose polymer is selected from the group consisting of cellulose ethers and cellulose esters.

3. A tablet according to claim 2 wherein the cellulose polymer is hydroxypropyl methyl cellulose.

4. A tablet according to claim 1 wherein the binder is microcrystalline cellulose.

5. A tablet according to claim 1 characterized in that it shows a release of tolcapone such that not greater than 90% is released during the period starting with oral ingestion and ending 5 hours after oral ingestion.

6. A tablet according to claim 1 comprising tolcapone, hydroxypropylmethyl cellulose and microcrystalline cellulose.

7. A tablet according to claim 6 comprising tolcapone, hydroxypropylmethyl cellulose, microcrystalline cellulose, talc, magnesium stearate and anhydrous colloidal silica.

8. A tablet according to claim 7 comprising by weight of the tablet:
 a) 30% to 50% tolcapone,
 b) 20 to 36% hydroxypropylmethyl cellulose,
 c) 36 to 49% microcrystalline cellulose,
 d) 0.1 to 3% talc,
 e) 0.03 to 2% magnesium stearate, and
 f) 0.06 to 0.8% by weight of anhydrous colloidal silica.

9. A method for the treatment of a transthyretin-associated amyloidosis comprising administering to a subject in need thereof an effective amount of a tablet according to claim 1.

10. A process for the manufacture of a tablet of claim 1 comprising:
 a) providing tolcapone, a release retardant and a binder,
 b) optionally sieving the ingredients of step a) with a mesh having 5 mm openings, c) mixing the ingredients of step b),
d) compressing the ingredients of step c) to form tablets, and
e) coating the tablet.

\* \* \* \* \*